(12) United States Patent
Okajima et al.

(10) Patent No.: US 11,832,978 B2
(45) Date of Patent: Dec. 5, 2023

(54) X-RAY COMPUTED TOMOGRAPHY APPARATUS AND CONTROL METHOD (71) Applicant: CANON MEDICAL SYSTEMS CORPORATION, Otawara (JP)

(72) Inventors: Yuji Okajima, Otawara (JP); Akihiro Ishida, Nasushiobara (JP); Hiroaki Miyazaki, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 64 days.

(21) Appl. No.: 17/644,673

(22) Filed: Dec. 16, 2021

(65) Prior Publication Data
US 2022/0202383 A1 Jun. 30, 2022

(30) Foreign Application Priority Data
Dec. 24, 2020 (JP) ................................. 2020-214717

(51) Int. Cl.
A61B 6/00 (2006.01)
A61B 6/03 (2006.01)

(52) U.S. Cl.
CPC ............ A61B 6/4241 (2013.01); A61B 6/032 (2013.01); A61B 6/4266 (2013.01); A61B 6/5205 (2013.01)

(58) Field of Classification Search
CPC ..... A61B 6/4241; A61B 6/032; A61B 6/4266; A61B 6/5205; A61B 6/4233
See application file for complete search history.

(56) References Cited

U.S. PATENT DOCUMENTS

| 10,217,246 | B2* | 2/2019 | Takayama | ............... | A61B 6/032 |
| 2013/0301890 | A1* | 11/2013 | Kaempfer | ............ | H04N 19/194 |
| | | | | | 382/131 |
| 2016/0022243 | A1* | 1/2016 | Nakai | .................. | A61B 6/4085 |
| | | | | | 378/5 |

FOREIGN PATENT DOCUMENTS

| JP | 2015-181627 A | | 10/2015 | | |
| JP | 2015181627 A | * | 10/2015 | | |
| JP | 2017202308 A | * | 11/2017 | ............. | A61B 6/032 |

* cited by examiner

Primary Examiner — David P Porta
Assistant Examiner — Casey Bryant
(74) Attorney, Agent, or Firm — Oblon, McClelland, Maier & Neustadt, L.L.P.

(57) ABSTRACT

An X-ray computed tomography apparatus according to an embodiment includes an X-ray detector and a processing circuitry. The X-ray detector includes a plurality of detection elements arranged in a plurality of rows at least in a channel direction. The processing circuitry acquires an estimated count number of X-rays incident on the X-ray detector for each of the plurality of detection elements and determines a bit number for transmission for detection data indicating a count number of each of the plurality of detection elements based on the estimated count number.

11 Claims, 6 Drawing Sheets

| | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| CASE 1  | | | | | | | | | | | | | | | | 1 |
| CASE 2  | | | | | | | | | | | | | | | 1 | 0 |
| CASE 3  | | | | | | | | | | | | | | 1 | 0 | 0 |
| CASE 4  | | | | | | | | | | | | | 1 | 0 | 0 | 0 |
| CASE 5  | | | | | | | | | | | | 1 | 0 | 0 | 0 | 0 |
| CASE 6  | | | | | | | | | | | 1 | 0 | 0 | 0 | 0 | 0 |
| CASE 7  | | | | | | | | | | 1 | 0 | 0 | 0 | 0 | 0 | 0 |
| CASE 8  | | | | | | | | | 1 | 0 | 0 | 0 | 0 | 0 | 0 | 0 |
| CASE 9  | | | | | | | | 1 | 0 | 0 | 0 | 0 | 0 | 0 | 0 | 0 |
| CASE 10 | | | | | | | 1 | 0 | 0 | 0 | 0 | 0 | 0 | 0 | 0 | 0 |
| CASE 11 | | | | | | 1 | 0 | 0 | 0 | 0 | 0 | 0 | 0 | 0 | 0 | 0 |
| CASE 12 | | | | | 1 | 0 | 0 | 0 | 0 | 0 | 0 | 0 | 0 | 0 | 0 | 0 |
| CASE 13 | | | | 1 | 0 | 0 | 0 | 0 | 0 | 0 | 0 | 0 | 0 | 0 | 0 | 0 |
| CASE 14 | | | 1 | 0 | 0 | 0 | 0 | 0 | 0 | 0 | 0 | 0 | 0 | 0 | 0 | 0 |
| CASE 15 | | 1 | 0 | 0 | 0 | 0 | 0 | 0 | 0 | 0 | 0 | 0 | 0 | 0 | 0 | 0 |
| CASE 16 | 1 | 0 | 0 | 0 | 0 | 0 | 0 | 0 | 0 | 0 | 0 | 0 | 0 | 0 | 0 | 0 |
| CASE 17 | 0 | 0 | 0 | 0 | 0 | 0 | 0 | 0 | 0 | 0 | 0 | 0 | 0 | 0 | 0 | 0 |

QUANTUM NOISE — EFFECTIVE SIGNAL BIT

FIG.8

| | 0 | 1 | 2 | 3 | 4 | 5 | 6 | 7 | 8 | 9 |
|---|---|---|---|---|---|---|---|---|---|---|
| CASE 1  | | | | | | | | | | 1 |
| CASE 2  | | | | | | | | | 1 | 0 |
| CASE 3  | | | | | | | | | 1 | 0 |
| CASE 4  | | | | | | | | 1 | 0 | 0 |
| CASE 5  | | | | | | | | 1 | 0 | 0 |
| CASE 6  | | | | | | | 1 | 0 | 0 | 0 |
| CASE 7  | | | | | | | 1 | 0 | 0 | 0 |
| CASE 8  | | | | | | 1 | 0 | 0 | 0 | 0 |
| CASE 9  | | | | | | 1 | 0 | 0 | 0 | 0 |
| CASE 10 | | | | | 1 | 0 | 0 | 0 | 0 | 0 |
| CASE 11 | | | | | 1 | 0 | 0 | 0 | 0 | 0 |
| CASE 12 | | | | 1 | 0 | 0 | 0 | 0 | 0 | 0 |
| CASE 13 | | | | 1 | 0 | 0 | 0 | 0 | 0 | 0 |
| CASE 14 | | | 1 | 0 | 0 | 0 | 0 | 0 | 0 | 0 |
| CASE 15 | | 1 | 0 | 0 | 0 | 0 | 0 | 0 | 0 | 0 |
| CASE 16 | 1 | 0 | 0 | 0 | 0 | 0 | 0 | 0 | 0 | 0 |
| CASE 17 | 0 | 0 | 0 | 0 | 0 | 0 | 0 | 0 | 0 | 0 |

FIG.9

ND CONTROL METHOD

CROSS-REFERENCE TO RELATED APPLICATIONS

This application is based upon and claims the benefit of priority from Japanese Patent Application No. 2020-214717, filed on Dec. 24, 2020; the entire contents of which are incorporated herein by reference.

FIELD

Embodiments described herein relate generally to an X-ray computed tomography apparatus and a control method.

BACKGROUND

Conventionally, in a photon counting type X-ray computed tomography (CT) apparatus, four-dimensional data is collected in a column direction, a channel direction, a time direction, and an energy region (bin) of an X-ray detector. Therefore, photon counting type X-ray CT has a large data transmission amount and needs a long data transfer time as compared with integral type X-ray CT in which three-dimensional data excluding the energy bin is collected.

In such a circumstance, the data amount may be reduced by data compression. In the case of lossy compression, a high compression rate may be achieved as compared with lossless compression. However, when the compression rate is increased for lossy compression, there is a large gap between the data before compression and the data restored after compression becomes large, and there is a reduction in the image quality of the image generated using the restored data. For this reason, it has been difficult to reduce the data transmission amount while the image quality is maintained.

DETAILED DESCRIPTION

An X-ray computed tomography apparatus described in the embodiment below includes an X-ray detector and a processing circuitry. The X-ray detector includes a plurality of detection elements arranged in a plurality of rows at least in a channel direction. The processing circuitry acquires an estimated count number of X-rays incident on the X-ray detector for each of the plurality of detection elements and determines a bit number for transmission for detection data indicating a count number of each of the plurality of detection elements based on the estimated count number.

An X-ray computed tomography (CT) apparatus and a control method according to each embodiment will be described below with reference to the drawings. In the following description, the components having the same or substantially the same functions as those described for the already described figure will be denoted by the same reference numeral and the duplicated description thereof will be given only when needed. Even when the same parts are illustrated, the parts may be illustrated with different dimensions or ratios from each other in the drawings.

There are various types of X-ray computed tomography apparatuses (CT apparatuses) for third-generation CT, fourth-generation CT, etc., and any type is applicable to each embodiment. Here, the third-generation CT is a rotate/rotate-type in which an X-ray tube and a detector are integrally rotated around the subject. The fourth-generation CT is a stationary/rotate-type in which a large number of X-ray detection elements are arrayed in a ring shape and fixed and only an X-ray tube is rotated around the subject.

An X-ray CT apparatus described in the following embodiment is an apparatus capable of executing photon counting CT. Specifically, the X-ray CT apparatus described in the following embodiment is an apparatus that uses a photon counting type X-ray detector (photon counting type detector) to count the X-rays having transmitted through the subject so as to reconstruct X-ray CT image data. In the following embodiment, the scan conducted by the X-ray CT apparatus (hereinafter, also referred to as "imaging") refers to conventional scan or helical scan.

Figure 1:
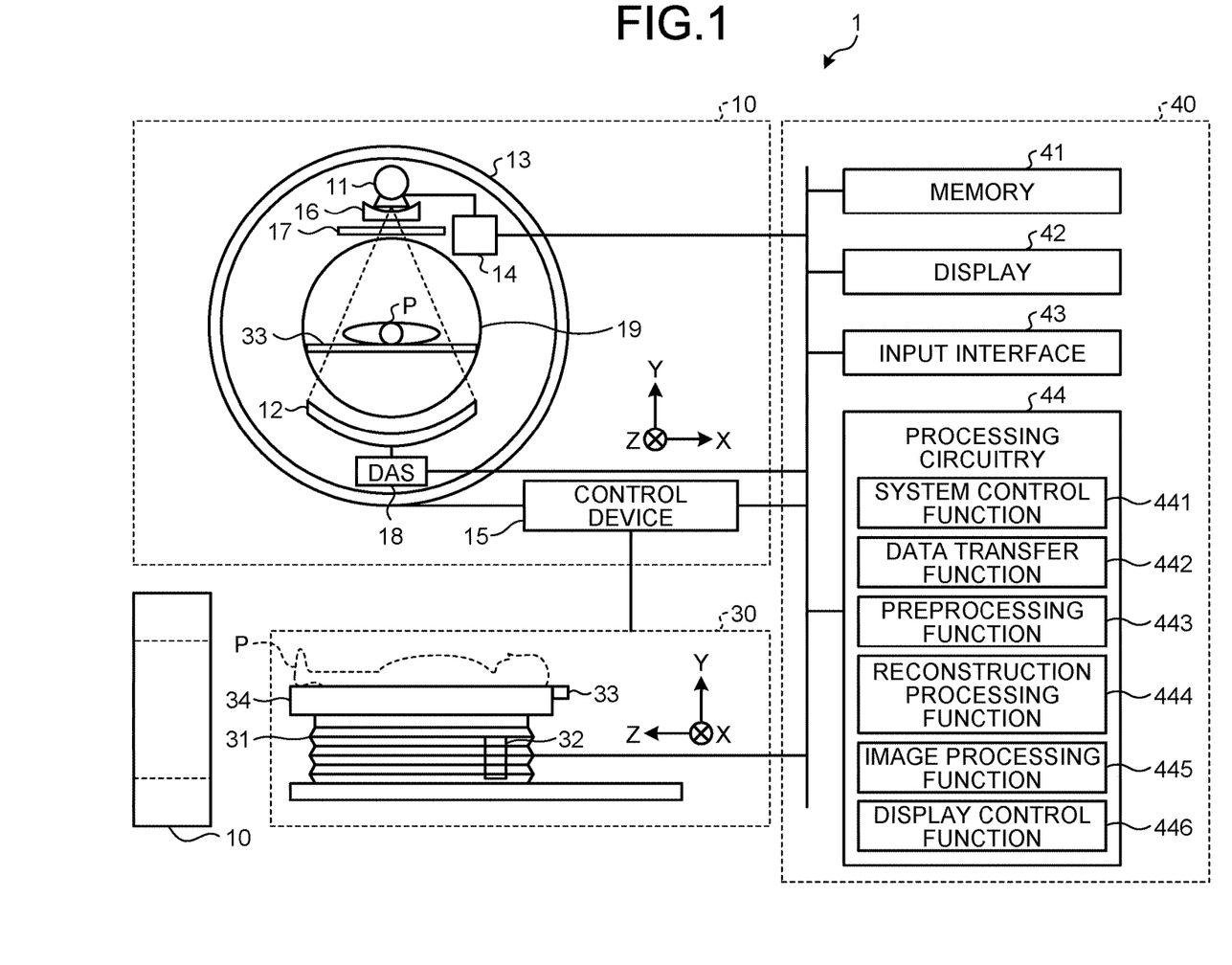
FIG. 1 is a diagram illustrating an example of a configuration of an X-ray computed tomography (CT) apparatus 1 according to an embodiment.

FIG. 1 is a diagram illustrating an example of a configuration of an X-ray computed tomography (CT) apparatus 1 according to an embodiment. The X-ray CT apparatus 1 irradiates a subject P with X-rays from an X-ray tube 11 and detects the irradiated X-rays with an X-ray detector 12. The X-ray CT apparatus 1 generates a CT image for the subject P based on an output from the X-ray detector 12.

As illustrated in FIG. 1, the X-ray CT apparatus 1 includes a gantry 10, a bed 30, and a console 40. The plurality of gantries 10 is illustrated in FIG. 1 for the convenience of explanation. The gantry 10 is a scanning device having a configuration for X-ray CT imaging of the subject P. The bed 30 is a transport device that has the subject P, which is the target of X-ray CT imaging, placed thereon to position the subject P. The console 40 is a computer that controls the gantry 10. For example, the gantry 10 and the bed 30 are installed in a CT examination room, and the console 40 is installed in a control room adjacent to the CT examination room. The gantry 10, the bed 30, and the console 40 are connected by wire or wirelessly so as to communicate with each other.

The console 40 does not necessarily need to be installed in the control room. For example, the console 40 may be installed in the same room together with the gantry 10 and the bed 30. The console 40 may be incorporated in the gantry 10.

According to the present embodiment, the rotation axis of a rotary frame 13 in a non-tilt state or the longitudinal direction of a top plate 33 of the bed 30 is defined as a Z-axis direction, the axial direction perpendicular to the Z-axis direction and horizontal to the floor surface is defined as an X-axis direction, and the axial direction perpendicular to the Z-axis direction and orthogonal to the floor surface is defined as a Y-axis direction.

As illustrated in FIG. 1, the gantry 10 includes the X-ray tube 11, the X-ray detector 12, the rotary frame 13, an X-ray high voltage device 14, a control device 15, a wedge 16, a collimator 17, and a data acquisition circuit (data acquisition system: DAS) 18.

The X-ray tube 11 is a vacuum tube including a cathode (filament) that generates thermoelectrons and an anode (target) that generates X-rays upon collision of thermoelectrons. The X-ray tube 11 uses a high voltage supplied from the X-ray high voltage device 14 to emit thermoelectrons from the cathode toward the anode and thus irradiate the subject P with X-rays. Here, the X-ray tube 11 is an example of an X-ray generation unit.

The hardware that generates X-rays is not limited to the X-ray tube 11. For example, instead of the X-ray tube 11, a fifth-generation method may be used to generate X-rays. The fifth-generation method includes a focus coil that focuses electron beams generated from an electron gun, a deflection coil that causes electromagnetic deflection, and a target ring that surrounds half the circumference of the subject P and generates X-rays due to collision of the deflected electron beams.

The X-ray detector 12 is a photon counting type detector that outputs a signal enabling measurement of the energy value of an X-ray photon each time the X-ray photon is incident. The X-ray photon is, for example, an X-ray photon emitted from the X-ray tube 11 and transmitted through the subject P. The X-ray detector 12 includes a plurality of detection elements that outputs one pulse of an electric signal (analog signal) each time an X-ray photon is incident. By counting the number of electric signals (pulses), the number (count number) of X-ray photons incident on each detection element may be counted. By performing arithmetic processing on the signal, the energy value of the X-ray photon that caused the output of the signal may be measured. For example, the X-ray detector 12 is a plane detector in which detection elements are arranged in N rows in a channel direction (the X-axis direction in FIG. 1) and in N rows in a column direction (the Z-axis direction in FIG. 1 or a slice direction).

The above-described detection element includes, for example, a scintillator and an optical sensor such as a photomultiplier tube. In this case, the X-ray detector 12 is an indirect conversion type detector that converts the incident X-ray photon into a scintillator light by the scintillator and converts the scintillator light into an electric signal by the optical sensor such as photomultiplier tube. The above-described detection element is obtained by arranging electrodes in a semiconductor detection element such as cadmium telluride (CdTe) or cadmium zinc telluride (CdZnTe). In this case, the X-ray detector 12 is a direct conversion type detector that directly converts the incident X-ray photon into an electric signal.

The X-ray detector 12 includes the above-described detection elements and a plurality of processors such as application specific integrated circuits (ASICs) that is connected to the detection elements to count X-ray photons detected by the detection elements. The processor discriminates the individual charges output by the detection element to count the number of X-ray photons incident on the detection element. The processor performs arithmetic processing based on the magnitude of the individual charge to measure the energy of the counted X-ray photon. The processor outputs the count result of the X-ray photons as digital data to the DAS 18. Here, the X-ray detector 12 is an example of an X-ray detection unit.

The rotary frame 13 is an annular frame that supports the X-ray tube 11 and the X-ray detector 12 so as to face each other and rotates the X-ray tube 11 and the X-ray detector 12 by the control device 15 described below. An image field of view (FOV) is set in an opening 19 of the rotary frame 13. For example, the rotary frame 13 is a casting made of aluminum. In addition to the X-ray tube 11 and the X-ray detector 12, the rotary frame 13 may further support the X-ray high voltage device 14, the wedge 16, the collimator 17, the DAS 18, and the like. The rotary frame 13 may further support various components that are not illustrated in FIG. 1.

The X-ray high voltage device 14 includes a high voltage generation device and an X-ray control device. The high voltage generation device includes an electric circuit such as a transformer and a rectifier to generate a high voltage applied to the X-ray tube 11 and a filament current supplied to the X-ray tube 11. The X-ray control device controls the output voltage corresponding to the X-rays emitted by the X-ray tube 11. The high voltage generation device may be of a transformer type or an inverter type. The X-ray high voltage device 14 may be provided in the rotary frame 13 in the gantry 10 or in a fixed frame (not illustrated) in the gantry 10. The fixed frame is a frame that rotatably supports the rotary frame 13.

The control device 15 includes a drive mechanism such as a motor and an actuator and a processing circuitry having a processor, a memory, and the like, to control the drive mechanism. The control device 15 receives an input signal from an input interface 43, an input interface provided in the gantry 10, or the like, and controls operations of the gantry 10 and the bed 30. For example, in response to the input signal, the control device 15 controls the rotary frame 13 so as to rotate, controls the gantry 10 so as to tilt, and controls the bed 30 so as to operate. The control for tilting the gantry 10 is performed when the control device 15 rotates the rotary frame 13 around an axis parallel to the X-axis direction based on the inclination angle (tilt angle) information input via the input interface attached to the gantry 10. The control device 15 may be provided in the gantry 10 or in the console 40.

The wedge 16 is a filter that adjusts the X-ray dose emitted from the X-ray tube 11. Specifically, the wedge 16 is a filter that transmits and attenuates the X-rays emitted from the X-ray tube 11 so that the X-rays emitted from the X-ray tube 11 to the subject P have a predetermined distribution. For example, the wedge 16 is a wedge filter or a bow-tie filter and is configured by processing aluminum, or the like, so as to have a predetermined target angle and a predetermined thickness.

The collimator 17 limits the irradiation range of X-rays having passed through the wedge 16. The collimator 17 slidably supports a plurality of lead plates that shield X-rays and adjusts the form of a slit that is formed by the plurality of lead plates. The collimator 17 may be referred to as an X-ray diaphragm.

The DAS 18 generates detection data based on the count result input from the X-ray detector 12. The detection data is, for example, a sinogram. The sinogram is data in which the counting processing results incident on the respective detection elements are arranged with regard to the respective positions (hereinafter also referred to as view angles) of the X-ray tube 11. The sinogram is data in which the counting processing results are arranged in a two-dimensional Cartesian coordinate system having a view direction and a channel direction as axes. The DAS 18 generates a sinogram, for example, on a column-by-column basis in the slice direction of the X-ray detector 12. Here, the counting processing result is data that is assigned to the number of X-ray photons for each energy region (bin). For example, the DAS 18 counts the photons (X-ray photons) resulting from X-rays, which are emitted from the X-ray tube 11 and transmitted through the subject P, and discriminates the energy of the counted X-ray photon to obtain the counting processing result. The DAS 18 transfers the generated detection data to the console 40. The DAS 18 is implemented by, for example, a processor.

The detection data generated by the DAS 18 is transmitted from a transmitter including a light emitting diode (LED) and provided in the rotary frame 13 to a receiver including a photodiode and provided in a non-rotary portion (e.g., a fixed frame not illustrated in FIG. 1) of the gantry 10 via an optical communication and is transferred to the console 40. The method for transmitting data from the rotary frame 13 to the non-rotary portion of the gantry 10 is not limited to an optical communication, and any non-contact data transmission method or contact-type data transmission method may be adopted.

According to the present embodiment, the X-ray CT apparatus 1 having the photon counting type X-ray detector 12 mounted therein will be described as an example, but the technique according to the present embodiment may be implemented as the X-ray CT apparatus 1 having the integral type X-ray detector 12 mounted therein.

The bed 30 is a device on which the subject P, which is the target to be scanned, is placed and moved and includes a base 31, a bed drive device 32, the top plate 33, and a support frame 34. The base 31 is a chassis that supports the support frame 34 so as to move in a vertical direction. The bed drive device 32 is a drive mechanism that moves the top plate 33, on which the subject P is placed, in the longitudinal direction (the Z-axis direction) of the top plate 33 and that includes a motor, an actuator, and the like. The top plate 33 is a plate where the subject P is placed. The top plate 33 is provided on an upper surface of the support frame 34. The top plate 33 may be projected from the bed 30 toward the gantry 10 so that the whole body of the subject P may be captured. The top plate 33 is formed of, for example, a carbon fiber reinforced plastic (CFRP) having desired X-ray transmittivity and physical properties such as rigidity and strength. For example, the inside of the top plate 33 is hollow. The support frame 34 supports the top plate 33 so as to move in the longitudinal direction of the top plate 33. In addition to the top plate 33, the bed drive device 32 may move the support frame 34 in the longitudinal direction of the top plate 33.

The console 40 includes a memory 41, a display 42, the input interface 43, and a processing circuitry 44. Data communication is executed among the memory 41, the display 42, the input interface 43, and the processing circuitry 44 via a bus. Although the console 40 is described as a separate body from the gantry 10, the gantry 10 may include the console 40 or a part of components of the console 40. Here, the input interface 43 is an example of an input unit.

The memory 41 is implemented by a semiconductor memory device such as a random access memory (RAM) or a flash memory, a hard disk, an optical disk, etc. For example, the memory 41 stores projection data and reconstructed image data. For example, the memory 41 stores detection data under each scan condition and estimated data (estimated count number) of count results under each scan condition obtained during a preliminary collection process. For example, the memory 41 stores various programs. A storage area of the memory 41 may be in the X-ray CT apparatus 1 or in an external storage device connected via a network. Here, the memory 41 is an example of a storage unit.

The display 42 presents various types of information. For example, the display 42 outputs a medical image (CT image) generated by the processing circuitry 44, a graphical user interface (GUI) for receiving various operations from the operator, etc. Any various displays may be used as the display 42 as appropriate. For example, a liquid crystal display (LCD), a cathode ray tube (CRT) display, an organic electro luminescence display (OELD), or a plasma display may be used as the display 42.

The display 42 may be provided at any place in the control room. The display 42 may be provided in the gantry 10. The display 42 may be of a desktop type or may include a tablet terminal, or the like, which may wirelessly communicate with a main body of the console 40. One or more projectors may be used as the display 42.

The input interface 43 receives various input operations from the operator, converts the received input operation into an electric signal, and outputs the electric signal to the processing circuitry 44. For example, the input interface 43 receives, from the operator, a collection condition for collecting projection data, a reconstruction condition for reconstructing a CT image, or an image processing condition for generating a post-processing image from a CT image. For example, a mouse, a keyboard, a trackball, a switch, a button, a joystick, a touch pad, and a touch panel display may be used as the input interface 43 as appropriate. According to the present embodiment, the input interface 43 is not limited to the one including these physical operating parts. Examples of the input interface 43 include an electric signal processing circuitry that receives an electric signal corresponding to an input operation from an external input device provided separately from the apparatus and outputs the electric signal to the processing circuitry 44. The input interface 43 may be provided in the gantry 10. The input interface 43 may include a tablet terminal, or the like, which may wirelessly communicate with the main body of the console 40.

The processing circuitry 44 controls the overall operation of the X-ray CT apparatus 1. The processing circuitry 44 includes a processor and a memory such as a ROM and a RAM as hardware resources. The processing circuitry 44 executes a system control function 441, a data transfer function 442, a preprocessing function 443, a reconstruction processing function 444, an image processing function 445, a display control function 446, and the like, by a processor that executes a program loaded into a memory.

With the system control function 441, the processing circuitry 44 controls various functions of the processing circuitry 44 based on the input operation received from the operator via the input interface 43. As an example, the processing circuitry 44 controls the scan performed by the gantry 10. Specifically, the processing circuitry 44 controls the operations of the X-ray detector 12, the X-ray high voltage device 14, the control device 15, the DAS 18, and the bed drive device 32 to control a count result collection process on the gantry 10. For example, the processing circuitry 44 controls the positioning scan for collecting a positioning image (scano image) and a projection data collection process during imaging (primary scan) for collecting an image used for diagnosis.

With the system control function 441, the processing circuitry 44 performs a preliminary collection process. The processing circuitry 44 performs the preliminary collection process before the positioning scan and the primary scan. During the preliminary collection process, the processing circuitry 44 collects detection data under each scan condition in a state where the subject P is not placed on the top plate 33. The detection data is data indicating the count number of each energy bin of each detection element detected without passing through the subject P. The processing circuitry 44 stores the detection data under each scan condition obtained during the preliminary collection process as estimated data (estimated count number) in the memory 41. As the estimated count number is a count number estimated in a state where the subject P (object) is not placed, the estimated count number may be used regardless of the subject or the region of interest.

As the preliminary collection process (imaging) is performed before the primary scan, data transmission at a high transmission rate is not needed. Therefore, the data transmission for imaging does not need a data conversion process to remove a higher-order bit in accordance with the scan condition as in a data transmission process (see FIG. 5) according to the present embodiment.

During a bit-number optimization process, the processing circuitry 44 acquires the estimated count number for the designated scan condition from the memory 41 in accordance with the designated scan condition received from the operator via for example the input interface 43. The processing circuitry 44 feeds the acquired estimated count number to the data transfer function 442. Here, the processing circuitry 44 that performs the system control function 441 is an example of an acquisition unit.

With the data transfer function 442, the processing circuitry 44 designates the most significant bit (MSB) for transmission of the detection data from the DAS 18 based on the estimated count number acquired by the system control function 441. The processing circuitry 44 designates the most significant bit for transmission for each detection element, each view, and each energy bin. Here, the most significant bit for transmission is the bit position of the most significant bit of the data to be transmitted. The most significant bit for transmission is the bit position according to the estimated count number other than the most significant bit included in the bits of the detection data output from the DAS 18. That is, the most significant bit for transmission is a bit lower than the most significant bit of the detection data from the DAS 18. Furthermore, the most significant bit for transmission is a bit higher than the bit position corresponding to the estimated count number so that the count result may be transmitted without loss even when a count number larger than the estimated count number is counted during collection. In other words, the most significant bit for transmission is the bit position corresponding to the count number larger than the estimated count number. As described above, the processing circuitry 44 determines the bit number used for data transmission based on the estimated count number for each detection element, each view, and each energy bin. The processing circuitry 44 feeds the designated most significant bit to a conversion unit 21 (see FIG. 2) described below. Here, the processing circuitry 44 that performs the data transfer function 442 is an example of a determination unit.

With the preprocessing function 443, the processing circuitry 44 generates data by executing preprocessing such as logarithmic conversion processing, offset correction processing, sensitivity correction processing between channels, and beam hardening correction on the detection data output from the DAS 18. Data (detection data) before preprocessing and data after preprocessing are also collectively referred to as projection data below.

With the preprocessing function 443, the processing circuitry 44 performs a restoration process to, based on the most significant bit for data transfer designated by the data transfer function 442, divide the data (detection data) before preprocessing into data of each channel and reassigns a higher-order bit to restore the data into the original format. Here, the original format is, for example, the format of the data output from the DAS 18 and is a data format suitable for preprocessing and reconstruction processing. The processing circuitry 44 stores the restored data in the memory 41. Here, the processing circuitry 44 that performs the preprocessing function 443 is an example of a restoration unit.

With the reconstruction processing function 444, the processing circuitry 44 performs reconstruction processing using a filter correction back projection method, a successive approximation reconstruction method, machine learning, or the like, on the projection data having undergone preprocessing by the preprocessing function 443 to generate CT image data. The processing circuitry 44 stores the reconstructed CT image data in the memory 41.

Here, the projection data generated from the count result obtained by the photon counting type X-ray CT apparatus 1 includes information on the energy of the X-rays attenuated due to the transmission through the subject P. Therefore, with the reconstruction processing function 444, for example, the processing circuitry 44 may reconstruct the CT image data having a specific energy component. For example, the processing circuitry 44 may reconstruct CT image data having each of a plurality of energy components.

With the reconstruction processing function 444, the processing circuitry 44 may assign the color tone corresponding to an energy component to each pixel of the CT image data of each energy component and superimpose a plurality of sets of CT image data, which are color-coded in accordance with the energy components, to generate image data. For example, the processing circuitry 44 may use the K-absorption edge peculiar to a substance to generate the image data with which the substance may be identified. Examples of other image data generated by the processing circuitry 44 include monochromatic X-ray image data, density image data, and effective atomic number image data.

With the image processing function 445, the processing circuitry 44 uses a known method to convert the CT image data generated by the reconstruction processing function 444 into tomographic view data in any cross-section or three-dimensional image data based on the input operation received from the operator via the input interface 43. For example, the processing circuitry 44 performs three-dimensional image processing such as volume rendering, surface rendering, image value projection processing, multi-planar reconstruction (MPR) processing, and curved MPR (CPR) processing on the CT image data to generate rendering image data in any viewpoint direction. The reconstruction processing function 444 may directly generate three-dimensional image data such as rendering image data in any viewpoint direction. The processing circuitry 44 stores tomographic view data and three-dimensional image data in the memory 41.

With the display control function 446, the processing circuitry 44 presents an image on the display 42 based on various types of image data generated by the image processing function 445. The images presented on the display 42 include a CT image based on CT image data, a cross-sectional image based on cross-sectional image data in any cross-section, a rendering image in any viewpoint direction based on rendering image data in any viewpoint direction, etc. The images presented on the display 42 include an image for displaying an operation screen and an image for displaying a notification and a warning to the operator.

The system control function 441, the data transfer function 442, the preprocessing function 443, the reconstruction processing function 444, the image processing function 445, and the display control function 446 are not necessarily performed by a single processing circuitry. A plurality of independent processors may be combined to form the processing circuitry 44, and each of the processors may execute the respective programs to perform the system control function 441, the data transfer function 442, the preprocessing function 443, the reconstruction processing function 444, the image processing function 445, and the display control function 446. Here, the system control function 441, the data transfer function 442, the preprocessing function 443, the reconstruction processing function 444, the image processing function 445, and the display control function 446 may be implemented by being distributed or integrated in one or more processing circuitries as appropriate.

Although the single console 40 executes a plurality of functions in the description, different consoles may execute a plurality of functions. For example, functions such as the preprocessing function 443 and the reconstruction processing function 444 of the processing circuitry 44 may be distributed.

The processing circuitry 44 is not necessarily included in the console 40, but may be included in an integrated server that collectively processes the detection data acquired by a plurality of medical image diagnostic apparatuses.

Either the console 40 or an external workstation may execute post-processing. Both the console 40 and a workstation may simultaneously execute processing. For example, a processor that performs the reconstruction processing function 444 and the image processing function 445, a computer including a memory such as a ROM or a RAM as hardware resources, or the like, may be used as a workstation as appropriate.

Either a full-scan reconstruction method or a half-scan reconstruction method may be applied to the reconstruction of X-ray CT image data. For example, with the reconstruction processing function 444, the processing circuitry 44 uses projection data corresponding to the full circle around the subject P, i.e., 360 degrees, for the full-scan reconstruction method. The processing circuitry 44 uses the projection data corresponding to 180 degrees plus the fan angle for the half-scan reconstruction method. For the sake of simplicity of explanation, it is assumed below that the processing circuitry 44 uses the full-scan reconstruction method for reconstruction using the projection data corresponding to the full circle around the subject P, i.e., 360 degrees.

The technique according to the present embodiment is applicable to a single-tube type X-ray computed tomography apparatus and also what is called a multi-tube type X-ray computed tomography apparatus in which a plurality of pairs of an X-ray tube and a detector are mounted in a rotary ring.

The technique according to the present embodiment is also applicable to the X-ray CT apparatus 1 that is configured so as to execute imaging by a dual energy method. In this case, the X-ray high voltage device 14 may execute, for example, high-speed switching of two types of voltage values to alternately switch the energy spectra of X-rays emitted from the X-ray tube 11. That is, the X-ray CT apparatus 1 is configured so as to collect the projection data in each collection view while modulating the tube voltage at timing in accordance with the control signal for tube voltage modulation. By capturing the subject with different tube voltages, it is possible to improve the density contrast of the CT image based on the energy transmittivity of the substance for each X-ray energy spectrum.

Figure 2:
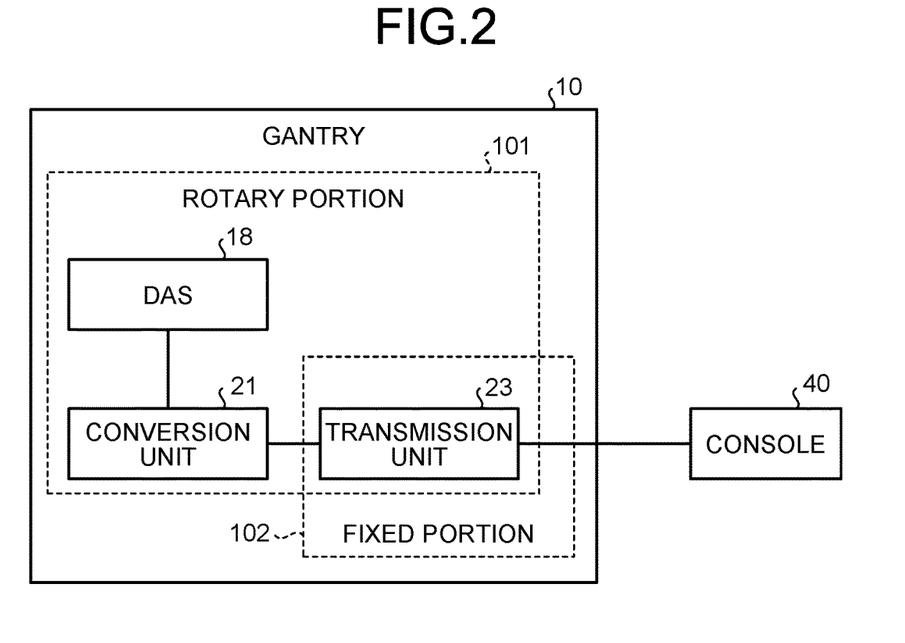
FIG. 2 is a diagram illustrating an example of a configuration for data transfer of the X-ray CT apparatus according to the embodiment.

FIG. 2 is a diagram illustrating an example of a configuration for the data transfer of the X-ray CT apparatus 1 according to the embodiment. As illustrated in FIG. 2, the gantry 10 includes a rotary portion 101 and a fixed portion 102.

The rotary portion 101 is a rotary portion of the gantry 10 and includes the rotary frame 13 and each unit of the gantry 10 supported by the rotary frame 13. The rotary Portion 101 includes the DAS 18 and the conversion unit 21. Here, the conversion unit 21 is an example of a converter.

The conversion unit 21 performs a data conversion process on the detection data from the DAS 18 to remove a higher-order bit of the detection data based on the most significant bit for transmission designated by the data transfer function 442. It is assumed that the data conversion process is performed for each detection element, each view, and each energy bin. Specifically, the conversion unit 21 removes a bit higher than the designated most significant bit for transmission from the detection data from the DAS 18. In other words, the conversion unit 21 removes a higher-order bit to convert the detection data from the DAS 18 into the detection data of the bit number determined by the data transfer function 442. The conversion unit 21 feeds the converted detection data to the transmitter of a transmission unit 23. The conversion unit 21 includes a processor and a memory such as a ROM and a RAM as hardware resources. The memory of the conversion unit 21 stores the most significant bit for data transmission designated by the data transfer function 442.

The fixed portion 102 is a non-rotary portion of the gantry 10, including a fixed frame that rotatably supports the rotary frame 13, the control device 15, etc.

The gantry 10 further includes the transmission unit 23. The transmission unit 23 transmits the detection data, and the like, from the rotary portion 101 to the fixed portion 102. As described above, the transmission unit 23 includes the transmitter provided in the rotary frame 13 and the receiver provided in the fixed frame, or the like. That is, the rotary portion 101 includes the transmitter of the transmission unit 23. The fixed portion 102 includes the receiver of the transmission unit 23. The receiver of the transmission unit 23 feeds the detection data received from the transmitter to the console 40.

The fixed portion 102 may include a restoration unit that executes the above-described restoration process, i.e., a part of the preprocessing function 443. The restoration unit includes a processor and a memory such as a ROM and a RAM that store the most significant bit for data transmission designated by the data transfer function 442 as hardware resources. When the transmission rate from the DAS 18 to the console 40 is limited due to the data transmission rate from the rotary portion 101 to the fixed portion 102, the data transmission rate during imaging may be improved even with this configuration. Specifically, it is applicable if the section between the conversion unit 21 and the restoration unit includes a section that is included in the data transmission section from the DAS 18 to the console 40 and is a bottleneck in the data transmission during imaging. Therefore, in the X-ray CT apparatus 1 according to the embodiment, the conversion unit 21 may be configured to be integral with the DAS 18 or the transmitter of the transmission unit 23. The restoration unit may be configured to be integral with the receiver of the transmission unit 23.

Figure 3:
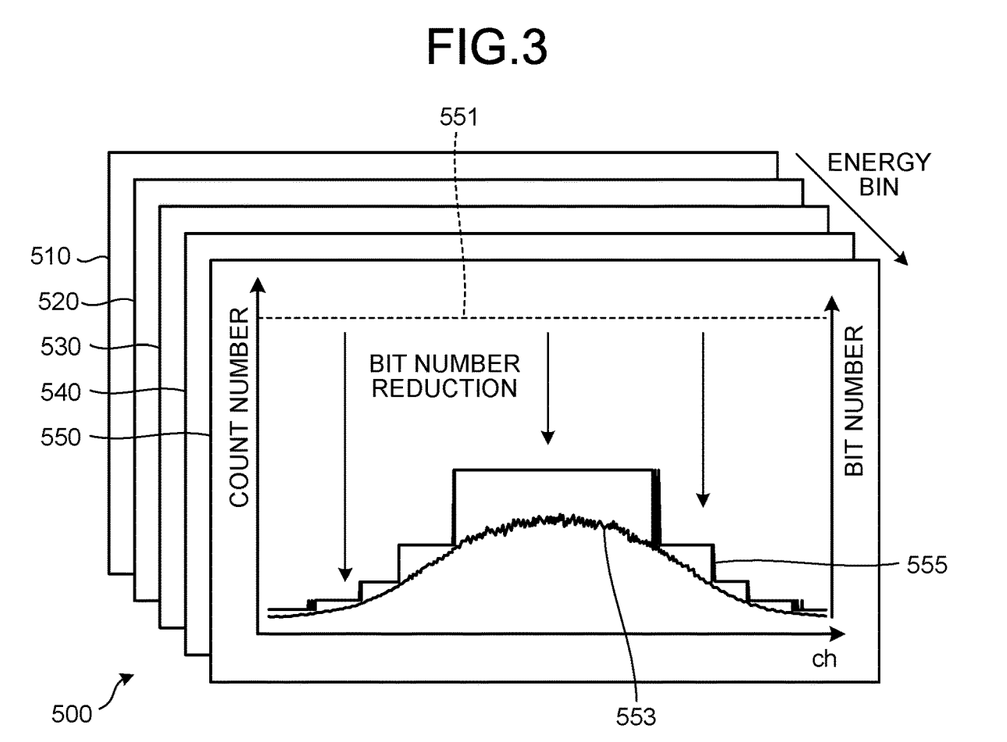
FIG. 3 is a diagram illustrating a reduction in a data transfer amount in the X-ray CT apparatus according to the embodiment.

Here, a reduction in the data transfer amount from the rotary portion 101 to the fixed portion 102 according to the embodiment will be described in more detail with reference to the drawings. FIG. 3 is a diagram illustrating a reduction in the data transfer amount in the X-ray CT apparatus 1 according to the embodiment. FIG. 3 illustrates detection data 500 from the DAS 18 at any view.

Each of the plurality of detection elements (pixels) of the X-ray detector 12 outputs a plurality of sets of data 510, 520, 530, 540, and 550 discriminated by an energy at each view. In the example illustrated in FIG. 3, the detection data 500 includes the five sets of data 510, 520, 530, 540, and 550 that are distributed to five energy bins. The description will be continued below by using the data 510 for any energy bin as an example.

Conventionally, the bit number of the detection data from the X-ray detector 12 (or the DAS 18) is a fixed value that is previously set in accordance with, for example, an expected output. A fixed value 551 is set to the bit number according to the count number 551 that is sufficiently larger than an expected count number 553 so as to reliably transmit the detection data 500 of the number of detected photons (the count number 553) that is expected under a plurality of scan conditions.

Therefore, for example, when the number of detected photons (count number) is small, higher-order bits of the detection data to be transmitted are sometimes not used under some scan condition. However, the higher-order bits are simply not used for representation of the count number but are transmitted as bits having the value "0" from the rotary portion 101 to the fixed portion 102. In such a circumstance, the data transmission from the rotary portion 101 to the fixed portion 102 in the transmission unit 23 has a low data transfer rate as compared with transmission in other sections, for example, sections for transmission by wire. Therefore, in the photon counting type X-ray CT apparatus 1 having a large amount of detection data, particularly, it takes a long time to transfer the data.

Therefore, in the X-ray CT apparatus 1 according to the present embodiment, the upper limit of the count number that may be measured under each scan condition is previously estimated, and higher-order bits that are not transmitted are set in such a range that the detection data 500 of a count number larger than the estimated count number may be transmitted. In the following description, the highest bit, which is a count number larger than the estimated count number and indicates the bit number sufficient for transmission of the detection data 500 of the estimated count number, is described as the most significant bit. That is, in the X-ray CT apparatus 1 according to the present embodiment, a bit higher than the most significant bit in the detection data from the DAS 18 is not transmitted. Thus, the data transfer amount may be reduced.

Here, it is estimated how much data transfer amount may be reduced by removing higher-order bits, i.e., how much data compression is possible by removing higher-order bits. In the following estimation, it is assumed that the view rate that may be measured by the X-ray CT apparatus 1 is 1000 to 5000 view/sec. It is assumed that the upper limit of the count number that may be counted by the X-ray detector 12 is 100 Mcps. It is assumed that the number of bins for energy discrimination is 5 bins. Further, it is assumed that the count number of each energy bin is identical.

First, the count number that may be counted by the X-ray detector 12 per view is the largest at 1000 view/sec, which is $1 \times 10^5$ count/view. At least 17 bits are needed to enable transmission of the detection data of 100,000 counts without compression. Therefore, conventionally, as described above, it is previously determined that the data of each energy bin of all the detection elements (pixels) is transmitted in 17 bits regardless of the scan condition.

Here, the transmission data amount per unit time and per detection element increases as the view rate increases. The amounts of data transmitted per detection element in the five energy bins are, for example, as follows.

1000 view/sec: $8.5 \times 10^4$ bit/pixel/sec
2000 view/sec: $1.7 \times 10^5$ bit/pixel/sec
3000 view/sec: $2.6 \times 10^5$ bit/pixel/sec
4000 view/sec: $3.4 \times 10^5$ bit/pixel/sec
5000 view/sec: $4.3 \times 10^5$ bit/pixel/sec In such a circumstance, a consideration is given to a case where higher-order bits are removed in accordance with the estimated count number. Here, the data transmission amount is calculated in a case where the data with the count of 50 Mcps by all the detection elements is given as the estimated detection data (estimated count number) of the X-ray detector 12.

The count number per view decreases as the view rate increases. For example, the count number that may be counted per view at 5000 view/sec is $1 \times 10^4$ count/view. As the count number is distributed to each energy bin, the count number for each bin is further reduced. As described above, when it is assumed that the same count number may be obtained for all the energy bins, the count number per energy bin is approximately $2 \times 10^3$ count/view. In this case, the bit number assigned to each energy bin is 11 bits.

Therefore, when the detection data collected at 5000 view/sec is to be transmitted, the bit number assigned to each energy bin may be reduced from 17 bits to 11 bits, so that it may be estimated that the amount of data to be transmitted is reduced by approximately 35%.

When the estimated count number is used, the bit number per detection element needed for transmission at each view rate may be estimated as follows.

1000 view/sec: $7.0 \times 10^5$ bit/pixel/sec
(Reduction rate of the bit number by removing higher-order bits: 18%)
2000 view/sec: $1.3 \times 10^5$ bit/pixel/sec
(Reduction rate of the bit number by removing higher-order bits: 24%)
3000 view/sec: $1.8 \times 10$ bit/pixel/sec
(Reduction rate of the bit number by removing higher-order bits: 30%)
4000 view/sec: $2.4 \times 10$ bit/pixel/sec
(Reduction rate of the bit number by removing higher-order bits: 30%)
5000 view/sec: $2.8 \times 10^5$ bit/pixel/sec
(Reduction rate of the bit number by removing higher-order bits: 35%)

As described above, in a case where the higher-order bits are removed in accordance with the estimated count number, even when the view rate is smaller than 5000 view/sec, the data size transmitted from the X-ray detector 12 to the console 40 may be reduced. According to the above estimation, the transmitted data may be reduced by approximately 20% to 40% in terms of the bit number per detection element needed for transmission at each view rate.

Figure 4:
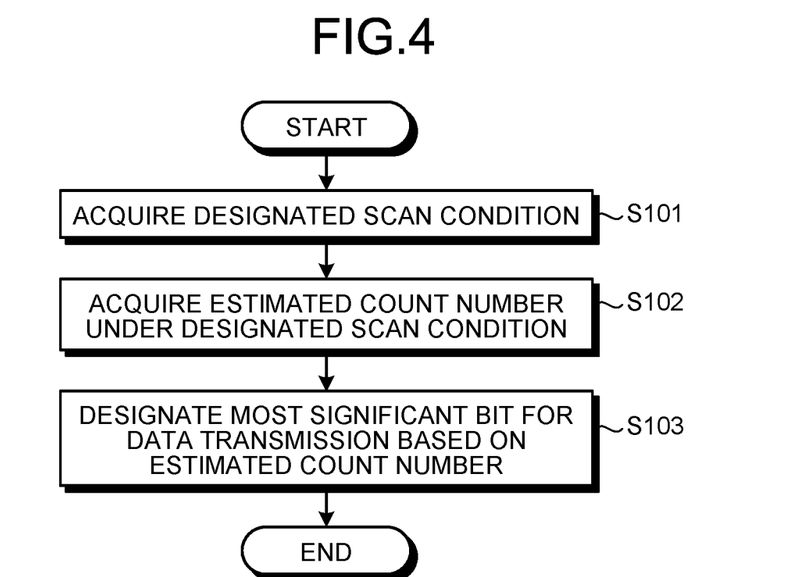
FIG. 4 is a flowchart illustrating an example of a bit-number optimization process performed by the X-ray CT apparatus according to the embodiment.

FIG. 4 is a flowchart illustrating an example of a bit-number optimization process performed by the X-ray CT apparatus 1 according to the embodiment.

With the system control function 441, the processing circuitry 44 acquires the scan condition of the primary scan designated by the operator based on the input operation received from the operator via the input interface 43 (S101). The processing circuitry 44 acquires the estimated count number under the acquired scan condition from the memory 41 (S102). The processing circuitry 44 feeds the acquired estimated count number to the data transfer function 442.

It is assumed that, prior to the process at S102, imaging (preliminary collection process) has been conducted under each scan condition in a state where the subject P is placed on the top plate 33.

With the data transfer function 442, the processing circuitry 44 designates the most significant bit for data transmission based on the estimated count number (S103). Specifically, the processing circuitry 44 determines the most significant bit for data transmission indicating the bit number that allows transmission of the detection data of the count number larger than the estimated count number for each detection element, each view, and each energy bin based on the estimated count number under each scan condition. The processing circuitry 44 feeds the determined most significant bit for data transmission to the conversion unit 21 of the rotary portion 101 of the gantry 10. Then, the flow of FIG. 4 ends.

As described above, during the bit-number optimization process according to the embodiment, the most significant bit for data transmission may be designated for each detection element, each view, and each energy bin so that different compression is performed for each detection element, each view, and each energy bin.

Figure 5:
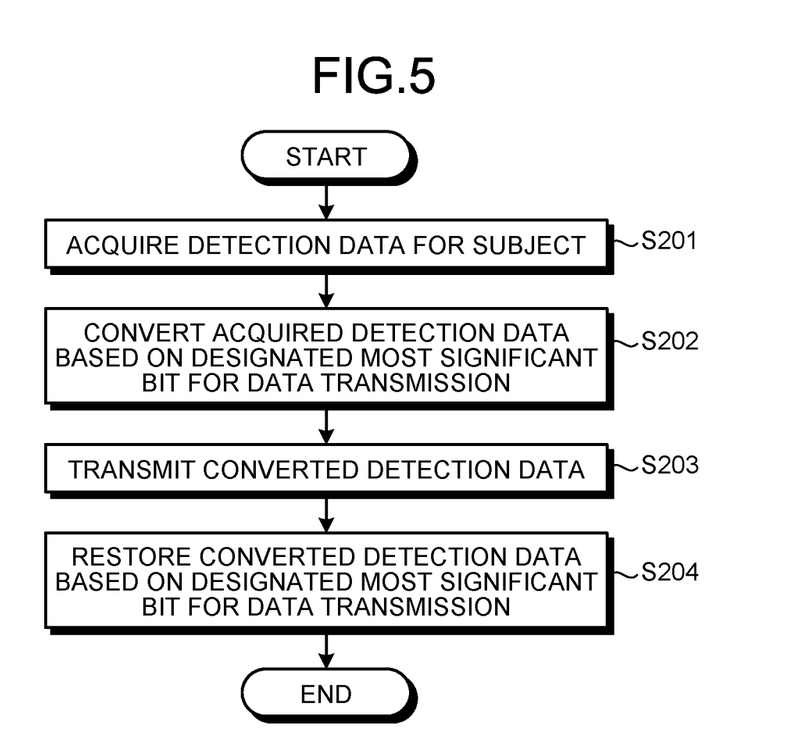
FIG. 5 is a flowchart illustrating an example of a data transmission process performed by the X-ray CT apparatus according to the embodiment.

FIG. 5 is a flowchart illustrating an example of a data transmission process performed by the X-ray CT apparatus 1 according to the embodiment. It is assumed that the flow of FIG. 5 is executed after the primary scan is started under the designated scan condition.

The conversion unit 21 acquires the detection data collected during the primary scan for the subject P from the DAS 18 (S201). The conversion unit 21 performs a data conversion process to convert the acquired detection data based on the most significant bit for data transmission designated by the data transfer function 442 during the bit-number optimization process (S202). The transmission unit 23 transmits the detection data converted by the conversion unit 21 (S203).

With the system control function 441, the processing circuitry 44 acquires the detection data converted by the conversion unit 21 and the most significant bit for transmission determined by the data transfer function 442 and feeds the detection data and the most significant bit for transmission to the preprocessing function 443. With the preprocessing function 443, the processing circuitry 44 performs a restoration process to restore the converted detection data based on the designated most significant bit for transmission (S204). Then, the flow of FIG. 5 ends.

As described above, during the data transmission process according to the embodiment, different data conversion (compression) may be performed for each detection element, each view, and each energy bin in accordance with the most significant bit for data transmission designated for each detection element, each view, and each energy bin with regard to the collected detection data.

As described above, in the X-ray CT apparatus 1 according to the embodiment, the X-ray detector 12 includes the plurality of detection elements arranged in a plurality of rows at least in the channel direction. The processing circuitry 44 acquires the count number (estimated count number) estimated for the X-rays incident on the X-ray detector 12 for each of the plurality of detection elements of the X-ray detector 12. Based on the acquired estimated count number, the processing circuitry 44 determines the bit number for data transmission of the detection data from the DAS 18 indicating the count number of each of the plurality of detection elements of the X-ray detector 12.

With this configuration, the bit number for data transmission may be reduced to the bit number according to the estimated count number acquired for each of the plurality of detection elements of the X-ray detector 12. Therefore, with the technique according to the embodiment, the time taken for data transfer may be reduced while the transmission image quality is maintained. A reduction in the time taken for data transfer contributes to a reduction in the time taken from imaging to image reconstruction completion and contributes to an improvement in inspection throughput.

As an example, in the X-ray CT apparatus 1 according to the embodiment, the processing circuitry 44 designates, as the most significant bit for transmission, the bit position according to the estimated count number other than the most significant bit included in the bits of the detection data from the DAS 18 and thus determines the bit number for transmission. Accordingly, the higher-order bits that do not contribute to the representation of the count result, that is, unnecessary higher-order bits, may be removed for transmission so that the amount of data to be transmitted may be reduced.

As an example, in the X-ray CT apparatus 1 according to the embodiment, the X-ray detector 12 is a photon counting type X-ray detector that outputs a plurality of sets of detection data discriminated by an X-ray energy for each view. The processing circuitry 44 determines the bit number for data transmission for each of the plurality of detection elements of the X-ray detector 12 at each view.

As an example, in the X-ray CT apparatus 1 according to the embodiment, the processing circuitry 44 acquires the detection data collected without transmission through the subject P under at least one scan condition and estimates the count number based on the acquired detection data. This makes it possible to calculate the estimated count number that may be used regardless of the object or the region of interest.

As an example, in the X-ray CT apparatus 1 according to the embodiment, the conversion unit 21 converts the bit number of the detection data, which is collected during the primary scan for the subject P and indicates the count number of each of the plurality of detection elements of the X-ray detector 12, into the bit number for data transmission. The transmission unit 23 transmits the converted detection data from the rotary portion 101 to the fixed portion 102. With the preprocessing function 443, the processing circuitry 44 restores the bit number of the converted detection data into the bit number before conversion by the conversion unit 21 for each of the plurality of detection elements of the X-ray detector 12 based on the bit number for data transmission. Thus, the detection data to be transmitted may be compressed, and the data amount of the detection data may be reduced.

First Modification

In the example described according to the above embodiment, the X-ray CT apparatus 1 calculates the estimated count number based on the detection data collected in a state where the subject P is not placed, but this is not a limitation. In the X-ray CT apparatus 1 according to the embodiment, the processing circuitry 44 may also calculate the estimated count number based on, for example, the data of the positioning image (scano image) of the subject P collected during positioning scan.

With the system control function 441, the processing circuitry 44 performs positioning scan (preliminary collection process) in accordance with the designated scan condition (S102). The processing circuitry 44 stores the scano image data, which is collected during the positioning scan and indicates the count number of each energy bin of each detection element, as estimated data (estimated count number) in the memory 41.

With this configuration, the calculated estimated count number may be made smaller than the estimated count number according to the above-described embodiment due to the attenuation of X-rays by the subject P. In other words, with the X-ray CT apparatus 1 according to the present modification, the bit number for data transmission in consideration of the shielding ability of the subject P may be determined. Thus, the X-ray CT apparatus 1 according to the present modification may compress the detection data to be transmitted more efficiently as compared with the X-ray CT apparatus 1 according to the above-described embodiment.

Second Modification

In the example described according to the first modification, the X-ray CT apparatus 1 calculates the estimated count number by using the scano image data to determine the bit number for data transmission in consideration of the shielding ability of the subject P, but this is not a limitation. In the X-ray CT apparatus 1 according to the embodiment, the processing circuitry 44 may calculate the estimated count number based on at least either the type or the shape of the wedge 16. The wedge 16 is provided between the X-ray tube 11, which generates X-rays, and the X-ray detector 12.

As an example, with the system control function 441, the processing circuitry 44 performs a preliminary collection process for each scan condition, each type of the wedge 16, and each shape of the wedge 16. The processing circuitry 44 stores, as estimated data (estimated count number) in the memory 41, the detection data for each scan condition, each type of the wedge 16, and each shape of the wedge 16 obtained during the preliminary collection process.

As another example, with the system control function 441, the processing circuitry 44 corrects the detection data under each scan condition obtained during the preliminary collection process according to the above-described embodiment based on at least either the type or shape of the wedge 16. That is, the processing circuitry 44 estimates the detection data for each type of the wedge 16 and each shape of the wedge 16 based on the X-ray shielding ability corresponding to the type and shape of the wedge 16. The processing circuitry 44 stores the estimated detection data (estimated count number) in the memory 41. The estimation of the detection data based on the type and shape of the wedge 16 may be performed during not only the preliminary collection process but also for example the process at S102 of FIG. 4.

With this configuration, even when the wedge 16 different from the wedge 16 used during data collection for correction, i.e., the preliminary collection process according to the above-described embodiment, is used during imaging, the estimated count number corresponding to the wedge 16 used during imaging may be calculated. In other words, with the X-ray CT apparatus 1 according to the present modification, the bit number for data transmission in consideration of the shielding ability of the wedge 16 may be determined. Thus, the X-ray CT apparatus 1 according to the present modification may compress the detection data to be transmitted more efficiently as compared with the X-ray CT apparatus 1 according to the above-described embodiment.

Third Modification

The X-ray CT apparatus 1 according to the present modification further includes an optical camera that captures the subject P placed on the top plate 33. The optical camera is provided on, for example, the chassis of the gantry 10. The optical camera may be provided on, for example, a ceiling of the CT examination room where the X-ray CT apparatus 1 is installed. The optical camera includes, for example, an imaging device capable of detecting visible light or infrared light.

In the X-ray CT apparatus 1 according to the present modification, the processing circuitry 44 may acquire, from an optical camera outside the X-ray CT apparatus 1, optical image data obtained by capturing the subject P placed on the top plate 33 with the optical camera. For example, the optical image data obtained by capturing the subject P in a standing position may be used as long as the physical constitution of the subject P may be determined based on the optical image data.

With the system control function 441, the processing circuitry 44 acquires the optical image data obtained by capturing the subject P with the optical camera. For example, the processing circuitry 44 performs image processing on the optical image data to acquire information on the physical constitution of the subject P such as the body thickness of the subject P in the image. Based on the information about the physical constitution of the subject P, the processing circuitry 44 estimates the transmission length of X-rays within the subject P detected in each view by each of the plurality of detection elements of the X-ray detector 12 and the attenuation rate of X-rays transmitted through the subject P. The processing circuitry 44 corrects the detection data corresponding to the designated scan condition during the preliminary collection process based on the transmission length and the attenuation rate of X-rays in the subject P. That is, the processing circuitry 44 estimates the detection data regarding the X-rays transmitted through the subject P based on the transmission length and the attenuation rate of the X-rays in the subject P.

Thus, it is possible to determine the bit number for data transmission in consideration of the shielding ability of the subject P corresponding to the physical constitution of the subject P such as the body thickness of the subject P.

Fourth Modification

The attenuation rate of X-rays transmitted through the subject P is estimated using a human body model so that the bit number for data transmission in consideration of the shielding ability of the subject P may be determined as in the third modification. With the system control function 441, the processing circuitry 44 acquires a human body model for the subject P from the memory 41 or from outside the X-ray CT apparatus 1. The processing circuitry 44 estimates, in the subject P, the transmission length and the attenuation rate of the X-rays incident on each of the plurality of detection elements based on the acquired human body model. Thus, the bit number for data transmission in consideration of the shielding ability of the subject P may be determined.

Fifth Modification

With the system control function 441, the processing circuitry 44 may also acquire the estimated count number by using a model having a determined parameter and configuration so as to calculate the estimated count number based on the scan condition, etc. The model includes a function having a determined parameter to output the estimated count number corresponding to each scan condition in response to the input of each scan condition and a table having registered therein the correspondence between each scan condition and the estimated count number. As an example, the estimated count number corresponding to each scan condition may be calculated based on each value corresponding to the configuration of the X-ray CT apparatus 1, such as the expected dose from the X-ray tube 11, the distance from the X-ray tube 11 to the X-ray detector 12, or the detection ability of the X-ray detector 12. For example, the model may be previously determined and stored in the memory 41.

The shielding ability of the subject P may be considered for generation of the model. In this case, a model is generated for, for example, each physical constitution (body shape) of the subject P. Alternatively, a model is generated for each imaging target portion of the subject P during the actual scan.

Even with these configurations, the bit number for data transmission in consideration of the shielding ability of the subject P may be determined.

Sixth Modification

Figure 6:
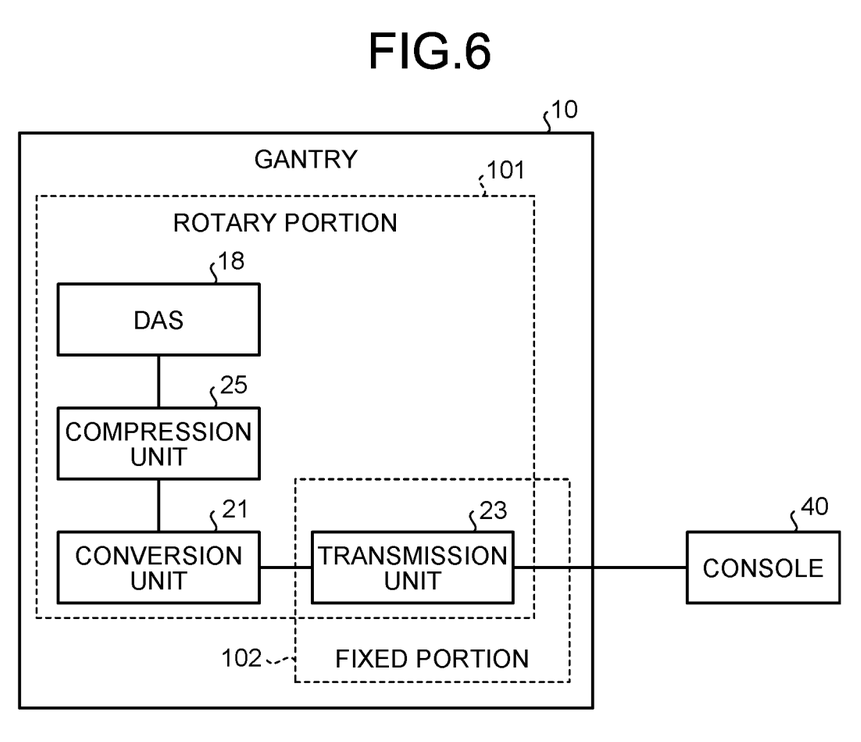
FIG. 6 is a diagram illustrating another example of the configuration for data transfer of the X-ray CT apparatus according to the embodiment.

FIG. 6 is a diagram illustrating another example of the configuration for data transfer of the X-ray CT apparatus 1 according to the embodiment. As illustrated in FIG. 6, in the X-ray CT apparatus 1, the rotary portion 101 may further include a compression unit 25. Here, the compression unit 25 is an example of a data compressor.

The compression unit 25 is provided after the DAS 18 and before the conversion unit 21. As an example, the compression unit 25 compresses the detection data collected for the subject P. The compression may be lossy compression (irreversible compression) or lossless compression. The conversion unit 21 removes the higher-order bits of the detection data compressed by the compression unit 25 to convert the bit number of the detection data into the bit number for data transmission designated by the data transfer function 442.

Figure 7:
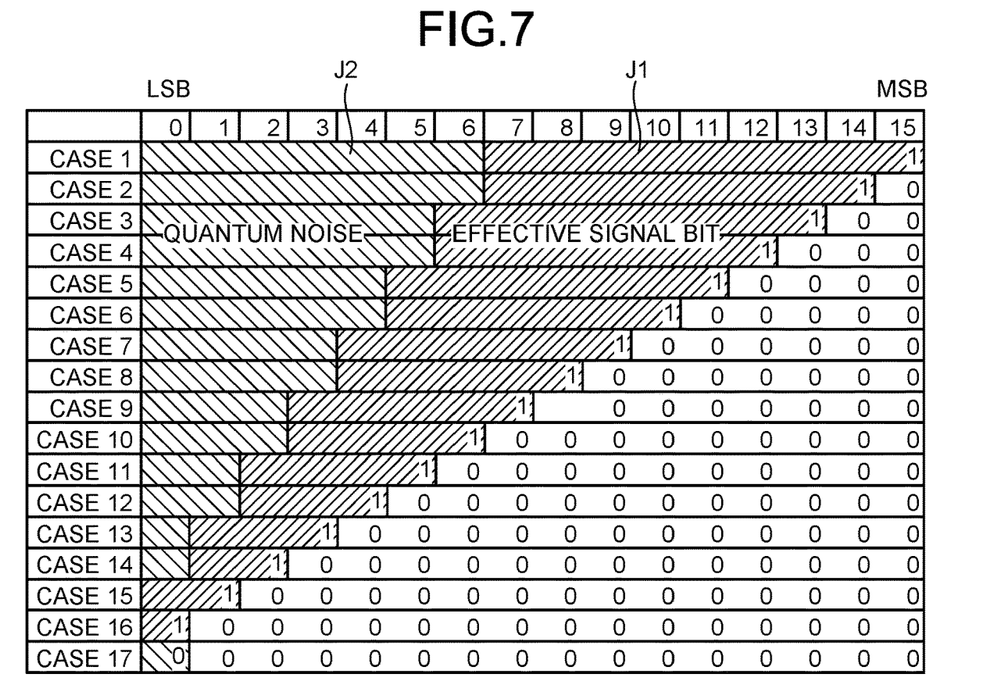
FIG. 7 is a diagram illustrating a compression process according to the embodiment.
Figure 8:
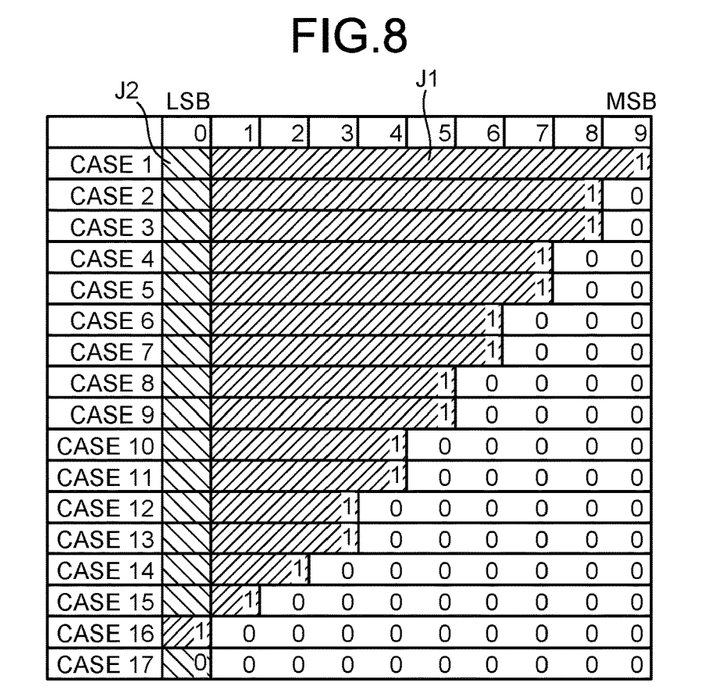
FIG. 8 is a diagram illustrating the compression process according to the embodiment.
Figure 9:
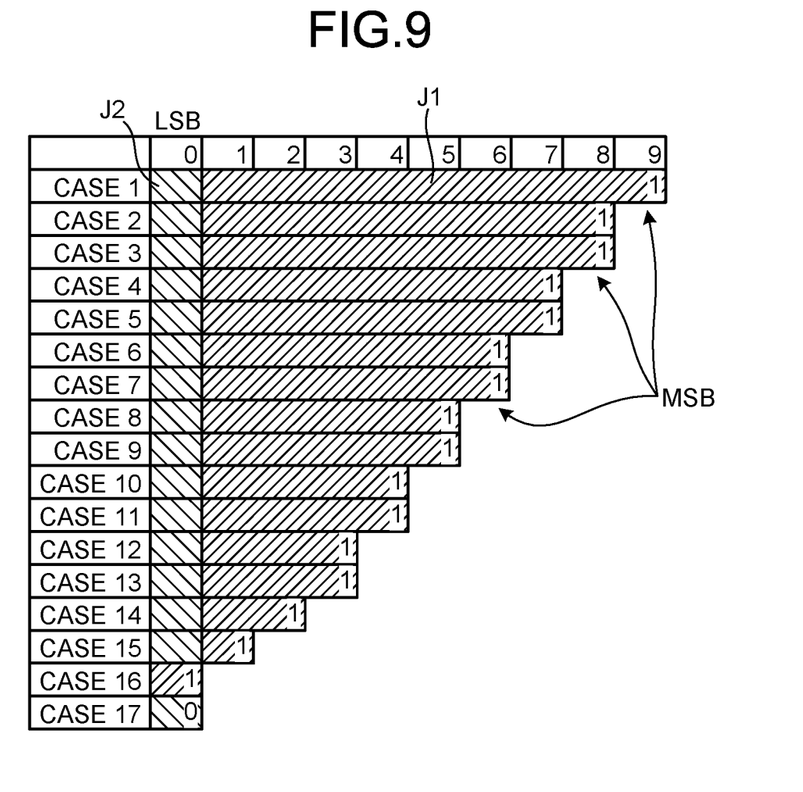
FIG. 9 is a diagram illustrating the compression process according to the embodiment.

FIGS. 7, 8 and 9 are diagrams illustrating the compression process according to the embodiment. FIG. illustrates the bit number of the data indicating the count number before data compression by the compression unit 25. FIG. 8 illustrates the bit number of the data indicating the count number after data compression by the compression unit 25. FIG. 9 illustrates the bit number of the data indicating the count number after the conversion unit 21 removes the higher-order bits of the data compressed by the compression unit 25. In the examples illustrated in FIGS. 7, 8 and 9, the horizontal axis indicates the bit number.

The data of the count number illustrated in FIG. 7 has a data length of 16 bits. Here, as illustrated in FIG. 7, a case is defined for each position of the most significant bit in which a predetermined bit value ("1" in FIG. 7) is input. Therefore, in the case of a data length of 16 bits, there are 17 cases including the case where the count is 0. In such a circumstance, lower-order bits of the data of the count number are bits J2, which are largely affected by quantum noise. With regard to the bits J2, which are largely affected by quantum noise, it is difficult to distinguish a change in the bit value from a quantum noise. In other words, the bits J2, which are largely affected by quantum noise, are unusable bits.

Therefore, the compression unit 25 according to the present modification removes the bits J2, which are largely affected by quantum noise, i.e., lower-order bits of the data of the count number, so as to suppress an increase in the data amount due to the presence of unusable bits. In other words, the compression unit 25 removes the lower-order bits to sequentially lower effective signal bits J1 and lower the most significant bit. FIG. 8 illustrates a case where the compression unit 25 removes the lower-order bits so that the data with the most significant bit in the 15th bit illustrated in FIG. 7 is irreversibly compressed to the data with the most significant bit in the 9th bit. For example, when the data illustrated in FIG. 8 is transmitted, the most significant bit (MSB) for transmission is the 9th bit.

The conversion unit 21 removes the higher-order bits of the data compressed by the compression unit 25 as illustrated in FIG. 9 in the same manner as in the above-described embodiment. Accordingly, the bit number of the data of the count number may be reduced as compared with the case where only lossy compression is applied, and the data amount of the detection data to be transmitted may be further suppressed. For example, when the data illustrated in FIG. 9 is transmitted, the most significant bit (NSF) for transmission is determined in accordance with the count number in each case and is the $9^{th}$ bit or less.

For the sake of simplicity of explanation, FIG. 9 illustrates a case where all the bits higher than the bit position of the most significant bit in which a predetermined bit value ("1" in FIG. 9) is input are removed. However, as described in the above embodiment, the most significant bit for transmission is the bit position corresponding to the count number larger than the estimated count number. Specifically, in the detection data to be transmitted, the bit value input to the most significant bit (NSF) for transmission is not always "1" but may be "0".

The technique according to each of the above-described modifications may be combined as appropriate to be applied to the X-ray CT apparatus 1 according to the embodiment.

The term "processor" used in the above description refers to, for example, a circuit such as a CPU, a GPU, an ASIC, or a programmable logic device (PLC). PLD includes a simple programmable logic device (SPLD), a complex programmable logic device (CPLD), and a field programmable gate array (FPGA). The processor reads and executes a program stored in a storage circuit to perform a function. The storage circuit storing the program is a computer-readable non-transitory recording medium. A configuration may be such that, instead of storing the program in the storage circuit, the program is directly installed in a circuit of the processor. In this case, the processor reads and executes the program installed in the circuit to perform the function. Instead of executing the program, the function corresponding to the program may be performed by a combination of logic circuits. Each processor according to the present embodiment is not always configured as a single circuit, but a plurality of independent circuits may be combined to form one processor and perform its function. The plurality of components in FIG. 1 may be integrated into one processor to perform its function.

According to at least one of the embodiments described above, the time taken for data transfer may be reduced while the image quality is maintained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus, comprising:
an X-ray detector including a plurality of detection elements arranged in a plurality of rows at least in a channel direction, the channel direction being orthogonal to a column direction; and
processing circuitry configured to
acquire an estimated count number of X-rays incident on the X-ray detector for each of the plurality of detection elements, and
determine a bit number for transmission for detection data indicating a count number of each of the plurality of detection elements based on the estimated count number,
wherein the processing circuitry is further configured to designate, as a most significant bit for transmission, a bit position according to the estimated count number other than a most significant bit included in bits of the detection data to determine the bit number for transmission.

2. The X-ray computed tomography apparatus according to claim 1, wherein
the X-ray detector is a photon-counting type X-ray detector that outputs a plurality of sets of detection data discriminated by an X-ray energy for each view, and
the processing circuitry is further configured to determine the bit number for transmission for the each view.

3. The X-ray computed tomography apparatus according to claim 1, wherein the processing circuitry is further configured to acquire detection data collected without transmission through a subject under at least one scan condition and indicating a count number of each of the plurality of detection elements, and calculate the estimated count number based on the acquired detection data.

4. The X-ray computed tomography apparatus according to claim 1, wherein the processing circuitry is further configured to acquire scano image data of a subject collected under at least one scan condition and calculate the estimated count number based on the acquired scano image data.

5. The X-ray computed tomography apparatus according to claim 1, wherein the processing circuitry is further configured to calculate the estimated count number based on at least either a type or shape of a wedge provided between the X-ray detector and an X-ray tube that generates the X-rays.

6. The X-ray computed tomography apparatus according to claim 1, wherein the processing circuitry is further configured to acquire optical image data of a subject acquired by an optical camera, acquire information on a physical constitution of the subject based on the acquired optical image data, estimate a transmission length and an attenuation rate of the X-rays in the subject based on information about the physical constitution of the subject, and calculate the estimated count number based on the transmission length and the attenuation rate.

7. The X-ray computed tomography apparatus according to claim 1, wherein the processing circuitry estimates is further configured to estimate a transmission length and an attenuation rate of the X-rays in a subject based on a human body model for the subject, and calculate the estimated count number based on the estimated transmission length and the attenuation rate.

8. The X-ray computed tomography apparatus according to claim 1, further comprising a memory that stores a model indicating a correspondence between the estimated count number and a scan condition, wherein
the processing circuitry is further configured to acquire a scan condition for collecting the detection data for a subject, and acquire the estimated count number from the memory based on the scan condition.

9. The X-ray computed tomography apparatus according to claim 1, further comprising:
a converter configured to remove a higher-order bit of the detection data collected for a subject to convert a bit number of the detection data into the bit number for transmission determined by the processing circuitry; and
a transmitter configured to transmit the converted detection data, wherein
the processing circuitry is further configured to assign a higher-order bit to the bit number of the transmitted detection data based on the bit number for transmission to restore the detection data to the bit number before conversion by the converter.

10. The X-ray computed tomography apparatus according to claim 9, further comprising a data compressor configured to perform lossy compression to remove a lower-order bit of the detection data collected for a subject, wherein
the converter is further configured to remove a higher-order bit of the detection data compressed by the data compressor to convert the bit number of the detection data into the bit number for transmission.

11. A control method, comprising:
acquiring a count number of X-rays incident on an X-ray detector including a plurality of detection elements arranged in a plurality of rows at least in a channel direction for each of the plurality of detection elements, the channel direction being orthogonal to a column direction; and
determining, based on the count number, a bit number for data transmission for each of the plurality of detection elements,
wherein the determining step further comprises designating, as a most significant bit for transmission, a bit position according to the estimated count number other than a most significant bit included in bits of the detection data to determine the bit number for transmission.

* * * * *